(12) United States Patent
Esteban et al.

(10) Patent No.: US 9,926,532 B2
(45) Date of Patent: Mar. 27, 2018

(54) METHOD OF GENERATING INDUCED PLURIPOTENT STEM CELLS AND DIFFERENTIATED CELLS

(75) Inventors: Miguel Esteban, Guangzhou (CN); Johannes Grillari, Bisamberg (AT); Regina Grillari, Bisamberg (AT); Duanqing Pei, Guangzhou (CN); Ting Zhou, Guangzhou (CN)

(73) Assignees: Guangzhou Institute of Biomedicine and Health, Guangzhou (CN); Universitat fur Bodenkultur Wien, Vienna (AT)

( * ) Notice: Subject to any disclaimer, the term of this patent is extended or adjusted under 35 U.S.C. 154(b) by 460 days.

(21) Appl. No.: 13/997,976

(22) PCT Filed: Dec. 23, 2011

(86) PCT No.: PCT/EP2011/073962
§ 371 (c)(1),
(2), (4) Date: Aug. 15, 2013

(87) PCT Pub. No.: WO2012/089669
PCT Pub. Date: Jul. 5, 2012

(65) Prior Publication Data
US 2013/0323782 A1 Dec. 5, 2013

Related U.S. Application Data

(63) Continuation-in-part of application No. PCT/CN2010/002226, filed on Dec. 31, 2010.

(30) Foreign Application Priority Data

Jan. 28, 2011 (EP) .................................. 11152519.2

(51) Int. Cl.
*C12N 5/00* (2006.01)
*C12N 5/02* (2006.01)
*C12N 5/074* (2010.01)
*C12N 5/0789* (2010.01)

(52) U.S. Cl.
CPC ......... *C12N 5/0696* (2013.01); *C12N 5/0647* (2013.01)

(58) Field of Classification Search
CPC .............................. C12N 5/0696; C12N 5/0647
See application file for complete search history.

(56) References Cited

U.S. PATENT DOCUMENTS 8,530,238 B2 * 9/2013 Yamanaka ........... C12N 5/0696
435/325

FOREIGN PATENT DOCUMENTS

| EP | 0780680 A2 | 6/1997 |
| WO | 2008-153685 A2 | 12/2008 |
| WO | 2009/032194 A1 | 3/2009 |
| WO | 2009/157201 A1 | 12/2009 |
| WO | 2009/157593 A1 | 12/2009 |
| WO | WO 2010036923 A1 * | 4/2010 ........... C12N 5/0696 |
| WO | 2010/065239 A1 | 6/2010 |
| WO | 2010/084275 A1 | 7/2010 |

OTHER PUBLICATIONS

Djuric and Ellis, 202, Stem Cell Research and Therapy, 2010,1:3.*
NIH (Stem Cells: Scientific Progress and Future Research Directions, Department of Health and Human Services, Chapter 1, pp. 14, Jun. 2001.*
Thomson et al. (PNAS, 92:7844-7848 (Aug. 1995).*
Vierbuchen T et al., 2010; Nature 463, 1035-1041.
Wally V et al., 2010; Hum Mol Genet 19, 4715-4725.
Wally Vet al., 2008; J Invest Dermatol 128, 568-574.
Warren R et al., 1992; J Invest Dermatol 98, 693-699.
Wieser et al., 2008; Am J Physiol Renal Physiol 295, F1365-1375.
Wilson KD et al., 2009; Stem Cells Dev 18:749-58.
Woltjen K et al., 2009, Nature 458:766-70.
Yakubov E et al., 2010; Biochem Biophys Res Commun 394, 189-193.
Yamanaka S and Blau HM, 2010; Nature 465, 704-712.
Yang Jet al., 2010; J Biol Chem 285, 40303-40311.
Ye L et al., 2009 Proc Natl Acad Sci USA Jun. 16;106 (24):9826-3.
Ye Z and Cheng L, 2010; Regen Med 5, 521-530.
Yu J et al., 2009; Science 324:797-801.
Zhang Y et al., 2008; J Urol 180, 2226-2233.
Zhao Y et al., Cell Stem Cell. Nov. 6, 2008;3(5):475-9.
Zhou Hongyan et al., Current Opinion in Hematology, Jul. 2010, vol. 17, No. 4, 2010, pp. 276-280.
Zhou Ting et al., Journal of the Amercian Society of Nephrology, vol. 22, No. 7, 2011, pp. 1221-1228.
Zwi L et al., 2009, Circulation 120, 1513-1523.
International Search Report for PCT/EP11/73962 dated Feb. 23, 2012, 5 pages.
Written Opinion for PCT/EP11/73962 dated Feb. 23, 2012, 6 pages.
International Preliminary Report on Patentability for PCT/EP11/73962 dated Jul. 11, 2013, 8 pages.
Extended European Search Report for EP Application No. 11152519.2 dated Jun. 28, 2011, 10 pages.
Aasen Trond et al., Nature Protocols, vol. 5, No. 2, 2010, pp. 371-382.
Bandaletova et al., 2002. Apmis 110, 239-246.
Bilousova G et al., Apr. 2011;131(4):857-64, Epub Dec. 9, 2010.
Brown M et al., 2010, PloS ONE, 2010, 5, 6, 1-9.
Cai J et al., 2010; J Biol Chem 285, 11227-11234.
Chan YC et al., 2009 J Cardiovasc Electrophysiol 20, 1048-1054.
Cho HJ et al., 2010; Blood 116, 386-395.

(Continued)

*Primary Examiner* — Valarie E Bertoglio
(74) *Attorney, Agent, or Firm* — Loza & Loza, LLP; Michael Fedrick (57) ABSTRACT

Methods for generating iPSCs and differentiated cells of interest by reprogramming donor cells that have been obtained in a non-invasive manner. In particular, the donor cells are exfoliated epithelial urine cells. The differentiated cells can be obtained by differentiation of the reprogrammed iPSCs or by direct reprogramming the urine cells.

9 Claims, 2 Drawing Sheets

(56) References Cited

OTHER PUBLICATIONS

Dimos JT et al. 2008 Science Aug. 29; 321(5893):1218-2.
Dörrenhaus A et al., Arch Toxicol 2000; 74, 618-626.
Ebert AD et al.; 2009 Nature Jan. 15; 457(7227):277-8.
Efe JA et al., 2011, Nat Cell Biol. Mar. 2011; 13(3):215-22.
Esteban MA et al., 2010; Cell Stem Cell 6, 71-79.
Han J et al., 2010; PLoS One. Aug. 19; 5(8):e12297.
Hanna J et al., 2007; Science 318, 1920-1923.
Huangfu D et al., 2008; Nat Biotechnol 26:1269-75.
Huangfu et al., 2008; Nat Biotechnol 26:795-7.
Ichida JK et al., 2009; Cell Stem Cell 5:491-503.
Jia F et al., 2010; Nat Methods Mar. 7(3):197-9.
Judson RL et al., 2009; Nat Biotechnol. May ; 27(5): 459-461.
Kim D et al., 2009; Cell Stem Cell 4:472-6.
Kowalska J et al, 2008, RNA. Jun. 2008;14(6):1119-31.
Lau F et al., 2009; F1000 Biol Rep. 1: 84.
Lee G et al., 2009 Sep. 17, 2009;461(7262):402-6.
Li R et al., Cell Stem Cell, Jul. 2, 2010;7(1):51-63.
Li W et al., Cell Stem Cell. Jan. 9, 2009;4(1):16-9.
Li Y et al., Cell Reprogram. Jun. 12(3):237-47.
Lian Q et al., 2010; Thromb Haemost 104, 39-44.
Lin T et al., 2009; Nat Methods 6:805-8.
Loh YH, et al., Cell Stem Cell. Jul. 2, 2010;7(1):15-9.
Marro S et al., Cell Stem Cell. Oct. 4, 2011;9(4):374-82.
Miyoshi K et al., Journal of Bioscience and Bioengineering, Elsevier, Amsterdam, NL, vol. 110, No. 3, 2010, pp. 345-350.
Ng KM et al., 2010; J Mol Cell Cardiol 48(6), 1129-1137.
Pankratz MT et al., 2007, Stem Cells 25, 1511-1520.
Park IH et al., Cell. Sep. 5, 2008;134(5):877-86.
Qin D et al., 2008; J Biol Chem; 283, 33730-33735.
Raya A et al., 2009 Nature Jul. 2; 460 (7251):53.
Sancho-Bru P et al., Journal of Hepatology, Munksgaard International Publishers, Copenhagen, DK, vol. 54, No. 1, 2011, pp. 98-108.
Seki T, et al., Cell Stem Cell. Jul. 2, 2010;7(1):11-4.
Shen et al., Progress in Biochemistry and Biophysics, 36(8), 950-960.
Shi Y et al., 2008; Cell Stem Cell 2:525-8.
Solanki A and Lee KB, 2010; Chembiochem 11(6), 755-757.
Soldner FSong 2009 Cell Res 1233 et al., 2009; Cell 136(5):964-77.
Song Z et al., 2009, Cell Res 19(11), 1233-1242.
Staerk J, et al., Cell Stem Cell. Jul. 2, 2010;7(1):20-4.
Sun N et al., 2010; Cell Cycle 9:5, 880-885.
Szabo E et al., 2010; Nature 468, 521-526.
Takahashi K and Yamanaka S, 2006; Cell 126:663-76.
Takeuchi JK et al., 2009; Nature 459, 708-711.
Tateishi et al., 2008; J Biol Chem 283(46):31601-7.
Vierbuchen T and Wernig M, 2011, Nat Biotechnol. 2011;29(10):892-907.
Bellantuono et al, "Progeroid syndromes: models for stem cell aging?" Biogerontology. Feb. 2012;13(1):63-75. doi: 10.1007/s10522-011-9347-2; 15 pages.
Benda et al, "Urine as a Source of Stem Cells", Adv. Biochem Eng Biotechnol., 2013, 129, pp. 19-23.
Graf et al, "Forcing cells to change lineages", Nature, 2009, vol. 462, p. 587-594.
Sharpless et al, "How stem cells age and why this makes us grow old", Molecular Cell Biology, 8, pp. 703-713Nat Rev Mol Cell Biol. Sep. 2007;8(9):703-13.
Wong et al, "Gene therapy, gene targeting and induced pluripotent stem cells: Applications in monogenic disease treatment", Biotechnology Advances, Elsevier Publishing, Barking, GB, vol. 29, No. 1, 2011, pp. 1-10 (published vol. 28, Issue 6, Nov.-Dec. 2010, pp. 715-724).

\* cited by examiner

METHOD OF GENERATING INDUCED PLURIPOTENT STEM CELLS AND DIFFERENTIATED CELLS

CROSS-REFERENCE TO RELATED APPLICATIONS

This application is the U.S. national stage of International Patent Application No. PCT/EP2011/073962, filed on Dec. 23, 2011 and entitled METHOD OF GENERATING INDUCED PLURIPOTENT STEM CELLS AND DIFFERENTIATED CELLS, and claims the benefit of priority under 35 U.S.C. § 120 from International Patent Application No. PCT/CN2010/002226, filed on Dec. 31, 2010, and also claims the benefit of priority under 35 U.S.C. § 119 from European Patent Application No. 11152519.2, filed on Jan. 28, 2011. The disclosures of the foregoing applications are incorporated herein by reference in their entirety.

The invention relates to induced pluripotent stem cells and differentiated cells and methods for generating them.

BACKGROUND OF THE INVENTION

Embryonic stem cells (ESCs) are cells derived from blastocysts obtained from in vitro fertilization that have the potential to self-renew and to differentiate into any mature cell type of a mammalian, e.g. human, body (this property is know as "pluripotency"). Under specific tissue culture conditions, ESCs can be maintained undifferentiated for prolonged periods of time without loosing their pluripotent characteristics. Because of these properties, ESCs have aroused enormous interest in regenerative medicine. Potentially, tissues derived from ESCs could be used for clinical treatment of humans (either acute conditions or genetic and degenerative diseases). ESCs could also be used for drug screening, for example to study tissue-specific susceptibility to treatments, and to model genetic diseases in vitro. However, severe ethical and practical (the risk of immune rejection) limitations have seriously hampered application of ESCs in the clinic and, in many countries, also the research.

The recent discovery that somatic cells can be transformed into iPSCs by means of exogenous factors (this method has also been termed "nuclear reprogramming by exogenous factors" (Takahashi and Yamanaka, Cell 2006; 126:663-76) has the potential to change the current perception of personalized medicine and can also provide valuable in vitro models of human diseases (Yamanaka and Blau, 2010; Nature 465, 704-712; Lian et al., 2010; Thromb Haemost 104, 39-44).

Remarkably, iPSCs are similar to ESCs and have the potential to be used in patient-specific treatments, thus avoiding the risk of immune rejection. Because of these characteristics, iPSCs have received great attention worldwide. The generation of iPSCs requires the collection of tissue from the donor, the expansion of the donor cells in vitro, and the exposure of the cells to a cocktail of exogenous factors that are provided to the cell as purified proteins, protein extracts, RNA molecules, non-integrating plasmids, viruses (e.g. retroviruses, lentiviruses, adenoviruses, Sendai viruses), with or without chemical cocktails and with variations in the cell culture conditions.

Application of these factors has the effect that colonies with an ESC-like morphology progressively emerge. These colonies represent iPSC colonies that can be picked and subsequently expanded and characterized to verify that their behavior is similar to ESCs.

So far, human iPSCs have been generated using donor cells from skin (fibroblasts and keratinocytes), amniotic fluid, extra-embryonic tissues (placenta and umbilical cord; (Cai et al., 2010; J Biol Chem 285, 11227-11234) cord blood, periosteal membrane, dental tissue, adipose tissue, neural stem cells, hepatocytes, amnion-derived mesenchymal stem cells and peripheral blood cells (Ye and Cheng, 2010; Regen Med 5, 521-530; Cai et al., 2010; J Biol Chem 285, 11227-11234). Reprogramming of cells from these tissues has been achieved with varied frequencies, indicating that the cell of origin ("donor cell") matters. Due to the heterogeneity of the donor cells currently used for iPSC generation, it is difficult to set standards for performing comparative tests with iPSCs and ESCs and to draw meaningful conclusions from the test results.

The ideal donor cell type for generating iPSCs should be easily accessible, easily reprogrammable, and universal (any age, sex, ethnic group, and body condition). Nowadays, dermal fibroblasts are among the most frequently used cell sources for reprogramming, but they require not only an uncomfortable biopsy that needs to be performed in an aseptic environment by a specialist, but also prolonged expansion prior to use. They also have risk of somatic cell mutations due to exposure to light and radiation, and the procedure is contraindicated in severe skin diseases or burns. Recently, three research groups achieved reprogramming of peripheral blood cells without need of $CD34^+$ cell mobilization was reported (Loh et al., 2010; Cell Stem Cell 7, 15-19; Seki et al., 2010; Cell Stem Cell 7, 11-14; Staerk et al., 2010; Cell Stem Cell 7, 20-24). Brown et al., 2010, PloS ONE, 2010, 5, 6, 1-9, describe the generation of T lymphocyte-derived iPSCs from peripheral blood. Since these procedures are minimally invasive, require small blood quantity and do not need prolonged cell culture, they represent a significant advance inspite of the fact that their efficiency is very low. However, the main donor cells used according to these reports are mature T-cells that bear specific T-cell receptor rearrangements, which is undesirable for certain potential clinical applications. Also, T-cells do not carry the complete genetic information that is required for unlimited differentiation into any cell type.

Besides, in rare cases, receiving/donating blood is not exempt from ethical concerns, for example because of religious beliefs, and may not be feasible in patients with infectious diseases, blood diseases, or immunodepression. In the latter context, conditions are to be considered that affect coagulation (e.g. hemophilia), leukemia and genetic or acquired (e.g. cancer and AIDS) immunodepression.

In search for reprogramming of new tissues, iPSCs have also been produced from mouse meningeal membrane (Qin et al., 2008; J Biol Chem; 283, 33730-33735) and mammary epithelial cells (Li et al., 2010; Cell Stem Cell 7, 51-63), and in humans from periosteum and adipose stem cells (Esteban et al., 2010; Cell Stem Cell 6, 71-79), umbilical cord matrix and placenta (Cai et al., 2010; J Biol Chem 285, 11227-11234).

SUMMARY OF THE INVENTION

To speed up progress towards future applications of the iPSC technology, it is desirable to provide iPSCs, as well as differentiated cells of any cell type, tissues or organoids derived therefrom, from donor cells that represent a universal source, as well as differentiated cells directly derived from such donor cells. Furthermore, since the isolation of donor cells for generating iPSCs according to methods of the prior art usually requires an invasive step to obtain the donor tissue of interest, the inventors sought to provide iPSCs derived from a non-invasive cell source and the methods for producing such iPSCs.

WO2008/153685 describes a method for producing a culture of urine progenitor cells (UPCs) by providing a urine sample and then isolating urine progenitor cells from the sample. The progenitor cells have the potential to further differentiate into other cell types.

For obtaining a culture of differentiated cells, WO2010/065239 suggests isolating stem cells from urine and then differentiating them into certain cell types.

Common to these methods is that differentiation of the obtained urine cells only allows for a limited number of cell types.

It has been an object of the invention to provide a method for obtaining, from a non-invasively obtained cell source, pluripotent cells with a differentiation capacity that is unlimited with respect to the ultimately generated cell type.

To solve the problem underlying the invention, the inventors considered the criteria that should be met by an ideal cell source to be isolated from individuals and then reprogrammed to iPSCs (which can differentiate to any specific cell type) or directly differentiated ("transdifferentiated", i.e. differentiated directly, without the intermediate step of iPSC generation) to specific cell types, tissues or organoids: the cells should be easily accessible with no or only a minimal associated risk, they should be available in sufficient quantities, universally present in both males and females (without restriction in terms of ethical concern, race, age, or the health or disease status), and they should be susceptible to reprogramming with good efficiency. The inventors surprisingly found that somatic cells, i.e. terminally differentiated cells, from a non-invasive source like urine, can be efficiently reprogrammed to iPSCs or specific cells or cell lineages of interest.

The invention relates to a method for generating differentiated cells of interest from donor cells of another cell type, comprising
  i) expanding cells from a cell source obtained from a donor in a non-invasive manner, wherein said cell source is selected from urine, feces, saliva, hair, nasal secrete, cerumen, lacrimal fluid or the vaginal tract, and
  ii) generating differentiated cells from said expanded cells by
    a) reprogramming said cells to become iPSCs and then differentiating the iPSCs into the cells of interest, or by
    b) directly reprogramming said cells to become a differentiated cell of interest.

According to a preferred embodiment, said donor cells obtained in step i) are exfoliated cell from the urinary tract that are present in urine (in the following, these cells are termed "urine cells").

In the following, iPSCs derived from urine cells are termed "UiPSCs" (if not otherwise stated, e.g. with regard to the use of UiPSCs, this term also encompasses iPSCs obtained from other non-invasively obtained donor cells).

In the embodiment according to which the cell source is urine, step i) can be performed according to methods known in the art, it usually comprises the sub-steps
  a) collecting urine from a donor,
  b) isolating exfoliated cells from the urine, and
  c) expanding said exfoliated cells.

The exfoliated cells ii) may be any cell type found in urine that is amenable to reprogramming.

According to certain embodiments, the exfoliated cells are epithelial cells, e.g. renal tubular cells like human exfoliated proximal tubular epithelial cells (HEPTECs).

According to other embodiments, the exfoliated cells are fibroblastoid cells.

According to further embodiments, the exfoliated cells are progenitor-like cells, enodothelial-like cells, smooth muscle-like cells or interstitial like cells as described by Zhang et al., 2008; J Urol 180, 2226-2233).

The cells ii) may also be exfoliated cancer cells, e.g. renal cancer or bladder cancer cells.

After urine collection, the urine cells are centrifuged and the cell type of interest e.g. HEPTECs or fibroblastoid cells, is enriched by growing the cells in a medium that favors their growth, thereby preventing the growth of cells of an unwanted cell type.

Such media are known from the literature and/or commercially available. By way of example, media specifically catering for the requirements of epithelial cells include but are not limited to Renal Epithelial Basal Medium (REBM) and SingleQuot Kit CC-4127 REGM, both available from Lonza, EpiGRO medium from Millipore, Renal Epithelial Cell Basal Medium (ATCC), other epithelial cell media including airway or mammary epithelial cell media, e.g. like those available from Lonza, ATCC, or Cellapplications, or a combination thereof. Similarly, the medium or media based on the one described by Wieser et al., 2008 (Am J Physiol Renal Physiol 295, F1365-1375).

An example for a medium suitable for enriching fibroblastoid cells from urine is FGM®-2 Fibroblast Growth Medium, also available from Lonza.

Besides urine cells, which are the preferred donor cells to be used in the method of the invention, other cells that have been obtained from a donor individual in a non-invasive way may be expanded and reprogrammed to become iPSCs, or directly differentiated to a cell type of interest, e.g. cells obtained from feces, saliva, hair, nasal secrete, cerumen, lacrimal fluid or the vaginal tract. Methods for isolating and expanding such cells are known in the art, e.g. for exfoliated cells from colon in feces (Bandaletova et al., 2002. Apmis 110, 239-246), or from dermal papilla cells from hair (Warren et al., 1992; J Invest Dermatol 98, 693-699).

Another useful cell source is the fluid which is, during hemodialysis, inserted into the peritoneal cavity to exchange substances with blood through blood vessels in the peritoneum, which allows the blood to be filtered in a "similar" way as in the kidney. This fluid can be collected and is known to contain many cells.

"Reprogramming" [(step ii), embodiment a)] is a term acknowledged in the field for transforming somatic cells into iPSCs by means of exogenous factors.

In the experiments of the present invention, reprogramming urine cells to UiPSCs was performed using retroviral vectors that deliver the four reprogramming factors Sox2, Oct4, Klf4, and c-Myc ("Yamanaka factors" or "Yamanaka cocktail"), as originally described by Takahashi and Yamanaka, 2006; Cell 126:663-76).

In principle, any reprogramming method may be used that is capable of transforming the donor cells, in particular urine cells, to iPSCs, in particular UiPSCs.

Reprogramming may be achieved by one or more factors selected from an Oct family gene, a Klf family gene, and a Sox family gene. Furthermore, the combination of factors may comprise one or more gene products of an Oct family gene, a Klf family gene, together with a cytokine. The cytokine can be at least one of basic fibroblast growth factor (bFGF) and stem cell factor (SCF).

Preferably, these factors are inserted in non-viral expression vectors that are introduced into a somatic cell.

If the UiPSCs, or differentiated cells thereof, are intended for therapeutic application, methods are used that do not employ oncogenes and/or do not involve integration of the reprogramming factor-encoding DNA into the individual's genomic DNA.

Therefore, preferred methods of the invention for generating UiPSCs or differentiated cells thereof, for therapeutic purposes do not employ lentiviruses or retroviruses or use viruses modified such that the risk of genomic integration of the transgenes and undesirable side effects associated with such integration are minimized or completely abolished. Also, it has to be considered that transgene integration bears the risk of insertional mutagenesis, which may be associated with tumorigenicity in the treated patient.

Preferred methods for generating UiPSCs for therapeutic application are those that avoid genomic integration of the reprogramming genes (reviewed by Sun et al., 2010; Cell Cycle 9:5, 880-885) and/or that avoid oncogenes like Klf4 or c-Myc, e.g.

- using Cre-recombinase excisable lentiviruses (Soldner et al., 2009; Cell 136:964-77);
- using OCT4, SOX2, and NANOG alone, omitting c-Myc and Klf4 (Li et al., 2010; Cell Reprogram. June 12(3): 237-47);
- achieving virus-free and transgene-free human iPS cell derivation by using or iP/EBNA1 (Epstein-Barr nuclear antigen-1)-based episomal vectors encoding the reprogramming factors Oct4, Sox2, Klf4, c-Myc, Nanog, Lin28 and SV40LT (Yu et al., 2009; Science 324:797-801);
- using a virus-free reprogramming technique using piggy-Bac transposon expression vectors carrying a polycistronic transgene of the Yamanaka factors (Woltjen et al., 2009, Nature 458:766-70); non-viral minicircle DNA (Jia et al., 2010; Nat Methods March 7(3):197-9);
- recombinant protein-based methods, e.g. treating the cells with the four Yamanaka factors in the form of recombinant proteins conjugated to a cell-penetrating peptide (cpp) (Kim et al., 2009; Cell Stem Cell 4:472-6); exposing the cells to a cocktail of exogenous factors that are provided to the cell as purified proteins, protein extracts with or without prior chemical treatment (Cho et al., 2010; Blood 116, 386-395; Han et al., 2010; PLoS One. August 19; 5(8):e12297; Solanki and Lee, 2010; Chembiochem 11, 755-757).
- adding small molecules, e.g. valproic acid, a histone deacetylase inhibitor (Huangfu et al., 2008; Nat Biotechnol 26:795-7; Huangfu et al., 2008; Nat Biotechnol 26:1269-75); or a number of other small molecules, e.g. inhibitors of glycogen synthase kinase 3 (GSK-3), MEK-ERK pathway and TGFβ pathway inhibitors to increase efficiency of or replace some of the reprogramming factors (Lin et al., 2009; Nat Methods 6:805-8; Li et al., 2009; Cell Stem Cell 4:16-9; Shi et al., 2008; Cell Stem Cell 2:525-8; Ichida et al., 2009; Cell Stem Cell 5:491-503); or adding vitamin C (Esteban et al., 2010; Cell Stem Cell 6, 71-79);
- adding small interfering RNAs (siRNAs), e.g. p53 siRNA, to improve efficiency of reprogramming by the Yamanaka factors (Zhao et al., 2008; 3: Cell Stem Cell 475-9);
- adding micro RNAs (miRNAs) to the reprogramming cocktails (e.g. Wilson et al., 2009; Stem Cells Dev 18:749-58; Judson et al., 2009; Nat Biotechnol. May; 27(5): 459-461).
- delivering mRNA, or modified mRNA, coding for reprogramming factors (Yakubov et al., 2010; Biochem Biophys Res Commun 394, 189-193), whereby, in the case of modification, it is such that it increases translation and/or stability, e.g. as described by Kowalska et al., 2008, RNA. 2008 June; 14(6):1119-31.

Safety/and or efficiency of reprogramming may be further optimized by changing the tissue culture medium or the environment, e.g. substitution of medium containing serum by Knock Out Serum Replacement (KSR, Invitrogen), or changing the environment (e.g. low oxygenation using specific incubators in which the oxygen concentration can be controlled).

Optimization can e.g. be achieved by doing serial experiments for a given expanded urine cell population. By way of example, urine cells from a number of individuals can be grown in different media (e.g. epithelial cell or fibroblast medium) prior to the infection with retroviruses producing the exogenous factors, in order to select for cell populations that are more easily reprogrammed. After infection, different cocktails of media are employed (with changes at different time points), serum-containing or serum-free, and with or without added chemicals (see above) to see under which conditions optimal efficiency can be achieved. Also, the cells can be infected with different combinations of factors, for example the 4 Yamanaka factors with or without Nanog (or other factors e.g. microRNAs). It can also be tested with how many rounds of infection (1, 2 or 3 rounds) the best results can be obtained. When the cells are split on feeder cells, different types of feeder layers can be used, e.g. mouse fibroblasts, human fibroblasts, amniocytes, amniotic membrane, etc.

Directly reprogramming the donor cell, without first generating an iPSC, to become a differentiated cell of interest [step ii), embodiment b)] is also known as "transdifferentiation", which means the change of a cell or tissue from one differentiated state to another (Vierbuchen and Wernig, 2011, Nat Biotechnol. 2011; 29(10):892-907.

In this embodiment, cell type-specific transcription factors are overexpressed using viral vectors, plasmid based vectors etc. as for the factors for iPS reprogramming.

For the direct transdifferentiation of urine cells (or other non-invasively obtained cells) into neurons, the 3 factors Ascl1, Brn2, and Myt11 may be used as described for the conversion of human fibroblasts to neurons (Vierbuchen et al., 2010; Nature 463, 1035-1041), or hepatocytes to neurons, as described by Marro et al., 2011, Stem Cell. Oct 4; 9(4):374-82.

Efe et al., 2011, Nat Cell Biol. 2011 March; 13(3):215-22, describe a method by which mouse embryonic fibroblasts (MEFs) can be directly reprogrammed to spontaneously contracting patches of differentiated cardiomyocytes.

For the conversion of urine donor cells to cardiomyocytes, a method may be used that has been successfully performed to obtain cardiomyocytes from mesoderm, using Gata4, Tbx5, and Baf60c (Takeuchi et al., 2009; Nature 459, 708-711).

The transdifferentiation to hematopoietic cells may be done by using Oct4 overexpression alone (Szabo et al., 2010; Nature 468, 521-526).

Screening for factors that transdifferentiate urine cells to neurons, keratinocytes, fribroblasts, cardiomyocytes, liver, kidney, blood cells etc. can be done similarly to the above-described transdifferentiation protocols and the initial Yamanaka protocol (Takahashi and Yamanaka, 2006). Based on the rich knowledge about lineage specific transcription factors, such factors can be tested in combinations (as in the articles described above) for their potential to directly transdifferentiate urine-derived cells in combination with cultivation conditions that are commonly used to maintain and cultivate the specific cell type of interest. Serial experiments according to the principles described above for optimizing reprogramming efficiency can also be done for optimizing transdifferentiation efficiency.

Although the method for of the invention is preferably used for producing UiPSCs or differentiated cells from human donor cells, it may also be applied to cells from other mammals (e.g. monkey, horse, dog, cat, pig, rat, and mouse).

Producing differentiated cells of interest, either directly or via the intermediate UiPSCs, from exfoliated urine cells, provides a universal easy-to reproduce-method for generating high quality ESC-like cells. It has the advantage that collection of the donor cells can be performed anywhere and by anyone, provided that minimal hygiene measures are taken, and from any human being irrespective of age, sex, or condition. In addition, the fluid perfused into the peritoneum for replacing lack of kidney function in patients with renal insufficiency who require dialysis, or patients after bladder operations who do not produce urine, can be used as a source of cells for reprogramming or transdifferentiation.

The method of the invention provides a unique chance to compare reprogramming methods worldwide and advance the field towards clinical application of safe iPSCs.

In principle, UiPSCs, or iPSCs obtained by the method of the invention from other non-invasively obtained donor cells, may be used for the same purposes as iPSCs known in the art generated from other cell types.

The advantageous characteristics of UiPSCs make them useful both from a research and a commercial perspective, the latter e.g. by providing UiPSCs, or cells, cell lineages, organoids or tissues, derived therefrom, from a healthy individual or a patient with a disease), e.g. for screening purposes.

UiPSCs can be used to generate cells for tissue repair or replacement while avoiding the ethical and immunological issues that are inherent in the use of ES cells.

UiPSCs of the invention, tissues, or organoids derived therefrom, respectively, are particularly useful for the treatment of patients with severe burns, who will be provided with artificial skin obtained from differentiated cells, derived from urine cells, either directly or via UiPSCs.

For the treatment of blood diseases, UiPSCs or differentiated cells obtained from them, or cells obtained by direct transdifferentiation of urine cells, can be infused into patients suffering from e.g. somatic mutation-induced leukemia.

In the treatment of hemophilia, genetically corrected UiPSCs can be used for autologous transplantation, and in case of diseases that diminish the amount of immune cells as e.g. in HIV, UiPSCs converted to hematopoietic cells can be used to replenish the immune cell population by infusion. In sickle-cell anemia, gene corrected iPS can also be used (Hanna et al., 2007; Science 318, 1920-1923).

UiPSCs (or iPSCs obtained from other non-invasively obtained donor cells) can be used, like the iPSCs known in the art, in the therapy of degenerative diseases, in which a specific cell type or tissue is destroyed or malfunctioning and the body is unable to replenish it. In degenerative conditions, e.g. Parkinson's disease, treatment with UiPSCs provides the affected site with undifferentiated cells that can then be used for repairing tissue damage. Thus, therapy with UiPSCs will reintroduce new healthy cells or tissue to fulfil the same function. UiPSCs also have the potential to be used to develop whole new organs which will be compatible with the patient and reduce the chances of transplant rejection since they are autologous cells, i.e. cells derived from donor cells of the patient to be treated, e.g. in the case of diabetes, insulin secreting islet like clusters can be generated like from iPSCs (Tateishi et al., 2008; Am J Physiol Renal Physiol 295, F1365-1375).

UiPSCs can also be used (as reviewed for iPSCs by Lau et al., 2009; F1000 Biol Rep. 1: 84) for the generation of disease-specific cell lines which are useful as disease models and/or for screening drug candidates in vitro and/or for correcting genetic defects by gene therapy. The generation of terminally differentiated cells (e.g. hepatocytes or cardiomyocytes) from UiPSCs (or obtained by transdifferentiation directly from urine cells) will for example allow the screening and further profiling of compounds on the respective cell lineage, with the objective of defining patient-specificity (for personalized medication) or general applicability of a compound. By way of example, as described by Dimos et al. 2008 (Science August 29; 321(5893):1218-2). UiPSCs can be used as a model for familial form of amyotrophic lateral sclerosis; or as a model, or for the treatment, respectively, of other genetic diseases, as described by Park et al., 2008 (Cell September 5; 134(5):877-8), who produced iPS cells from patients with 10 different genetic diseases, including Parkinson's disease, type-1 diabetes, Duchenne and Becker muscular dystrophy, adenosine deaminase deficiency-related severe combined immunodeficiency, Shwachman-Bodian-Diamond syndrome, Gaucher's disease type III, Huntington's disease, Down's syndrome, and the carrier state of Lesch-Nyhan syndrome. Also, human cell-based models of spinal muscular atrophy and Parkinson's disease can be generated similarly as described by Ebert et al.; 2009 (Nature January 15; 457(7227):277-8) and Soldner et al., 2009 (Cell. March 6; 136(5):964-77), or UiPSCs derived from cells from a patient with homozygous beta-thalassemia can be used similarly as described by Ye et al., 2009 (Proc Natl Acad Sci USA June 16; 106 (24):9826-3) for iPSCs derived from skin fibroblasts, which were subsequently differentiated into hemoglobin-producing hematopoietic cells. Such UiPSCs, upon genetic engineering, could yield autologous hematopoietic cells that function normally. UiPSCs can also be used to correct the genetic defects in Fanconi anemia patients, as described by Raya et al., 2009 (Nature July 2; 460 (7251):53), who derived iPS cells from dermal fibroblasts harvested from Fanconi anemia patients, corrected using lentiviral vectors encoding for FANCA and FANCD2, and subsequently derived somatic cells that were phenotypically disease-free.

UiPSCs can also be used like the iPS generated by Lee et al., 2009 (Nature September 17; 461(7262):402), who generated the iPSCs from patients with familial dysautonomia (FD), re-differentiated the iPS cells and used the in vitro model to screen candidate drugs.

Another example for a disease for which UiPSCs have potentially great value as a disease model, is Prader Willi syndrome (Yang et al., 2010; J Biol Chem 285, 40303-40311). Other examples of genetic diseases for which gene therapy using UiPSCs has great potential are Epidermolysis bullosa (e.g. by K14 mRNA reprogramming, as described by Wally et al., 2010; Hum Mol Genet 19, 4715-4725; Wally et al., 2008; J Invest Dermatol 128, 568-574). Generally, gene therapy based on genetically engineered UiPSCs has the greatest potential for treating diseases caused by single gene disorders; to date, ca. 4000 such genetic diseases have been described.

In the above disease models that use terminally differentiated cells, such cells can, alternatively to being obtained from UiPSCs, be obtained by direct reprogramming of the donor cells. For the purpose of the present invention "direct reprogramming" is used synonymously with "transdifferentiation", as defined herein.

If the donor cells are cancer cells, e.g. renal or bladder cancer cells, presumably representing early stages of the cancer, the UiPSCs or differentiated cells thereof are useful as models for the respective cancer.

Gene therapy comprises the insertion, alteration, or ablation of one or more genes within an individual's cells, to correct a genetic effect causing a disease. So far, mainly monogenic diseases, which are caused by mutations in single genes, have been considered for treatment. The most common form of gene therapy involves the insertion of functional genes into an unspecified genomic location in order to replace a mutated gene. A mutation may also be directly corrected.

For gene therapy applications, the genetically modified cells are UiPSCs or differentiated cells derived therefrom (or obtained by direct reprogramming of the donor cells); alternatively, albeit less preferred, the expanded donor cells may be genetically modified before reprogramming. In the scope of the invention, genetically modified cells are to be used prevalently in somatic gene therapy. Since the correction of the genetic defects is performed in vitro before re-infusing or transplanting the UiPSCs or differentiated cells derived therefrom (or obtained by direct reprogramming of the donor cells), the risk of gene transfer to the germline is minimized. The corrected cells will be infused or transplanted as differentiated cells derived from UiPSCs (or directly transdifferentiated without prior iPS reprogramming) in order to complement or replace non-functional tissue and organs. The correcting gene can be introduced into the cells according to methods known in the art, e.g. by viral vectors (modified to minimize the risk of reactivation) including retrovirus, adenovirus, adeno-associated virus, lentiviruses, Herpes simplex virus, by using plasmid-based vectors, or even naked DNA.

The correction of gene defects can be performed in many ways, e.g. by delivering DNA encoding the correctly functioning gene, by knocking down the mutated gene by delivering shRNA or miRNA, by using zinc finger proteins to perform knock-out or recombinations, or by using vectors that allow for trans-splicing events.

It may be anticipated that, due to the non-invasive way of obtaining donor cells, there may be a high acceptance by healthy individuals to have, in advance and prophylactically, prepared and stored UiPSCs derived from their own urine, as well as derived cell lineages, organoids or tissues like artificial skin, which will allow for a prompter use in the case of the emergence of a severe disease or an injury, like a burn.

Fibroblasts, keratinocytes or artificial skin generated from UiPSCs (Bilousova et al., 2010; J Invest Dermatol. December 9), e.g. derived from donor cells of individuals with different skin types, may also be useful in the cosmetics industry for testing.

UiPSCs may be also useful for cloning of animals, especially mammals, e.g. race horses or pets).

BRIEF DESCRIPTION OF THE FIGURES

FIG. 1

Hematoxylin/esosin stained slides of teratomas comprising complex derivatives of the 3 germ layers produced with 2 representative UiPSC clones

FIG. 2

A: Phase contrast and immunofluorescence photographs of neuronal-like cells produced following a reported protocol from a representative UiPSC clone.

B: A representative UiPSC clone was differentiated into cardiomyocyte-like cells using a reported protocol. Phase contrast, PAS staining and immunofluorescence photographs.

C: A representative UiPSC clone was differentiated into hepatocyte-like cells using a reported protocol. Phase contrast, PAS staining and immunofluorescence photographs.

D: Action potentials measured in cardiomyocytes derived from a representative UiPSC clone.

EXAMPLE

Materials and Methods
Immunofluorescence Microscopy

Cells were fixed in 4% paraformaldehyde overnight, washed, blocked and permeabilized in blocking solution (PBS containing 3% normal goat serum and 0.2% Triton X-100) for 30 minutes. Then they were incubated with primary antibodies in blocking solution at 4° C. overnight, washed twice and incubated with the corresponding secondary antibodies for 1 hour at room temperature. Cells were washed twice and stained with DAPI (Sigma) for 5 minutes, and then for observation and photographing using a Leica TCS SP2 Spectral confocal microscope (Leica Microsystems GmbH, Wetzlar, Germany). Before immunofluorescence, beating areas were cut out with scissors, collected into a 1.5 mL tube with low calcium PBS, and left for 30 minutes at room temperature. These cell clumps were transferred into enzyme buffer containing 0.5-1 mg/mL collagenase 2 and incubated at 37° for 30-40 minutes. The digestion was terminated with DMEM/Ham's F12 1:1 (Hyclone), 10% of fetal bovine serum (FBS; PAA), SingleQuot Kit CC-4127 REGM (Lonza). The samples were then centrifuged and the pellet resuspended in DMEM/Ham's F12 1:1 (Hyclone), 10% of fetal bovine serum (FBS; PAA), SingleQuot Kit CC-4127 REGM (Lonza). Cell suspensions were plated on gelatine-coated coverslips and cultured at 37° for at least 2 days before fixation and immunofluorescence.

Tissue-Specific Differentiation and Electrophysiological Measurements

Neuronal, hepatocyte and cardiomyocyte differentiation were performed as described (Pankratz et al., 2007, Stem Cells 25, 1511-1520; Song et al., 2009, Cell Res 19, 1233-1242; Zwi et al., 2009, Circulation 120, 1513-1523). N2 and B27 were purchased from Invitrogen, Heparin was purchased from Sigma, EGF were purchased from R&D Systems. Activin A and oncostatin M were purchased from R&D System (Minneapolis, Minn., USA), BMP2, FGF4, HGF and KGF from PeproTech (Rocky Hill, USA), and dexamethasone from Enzo Life Sciences (Farmingdale, USA). RPMI 1640, hepatoZYME-SPF, Periodic acid Schiff's (PAS) staining was performed using a kit purchased from Polysciences (Warrington, USA). Electrophysiological characterization of iPSC-derived cardiomyocytes (day 23) was done using standard whole-cell patch-clamp to record the action potential phenotypes (HEKA Instruments Inc., Southboro, Mass.) (Chan et al., 2009 J Cardiovasc Electrophysiol 20, 1048-1054). Patch pipettes were prepared from 1.5-mm thin-walled borosilicate glass tubes using a Sutter micropipette puller P-97 and had typical resistances of 3-5 MΩ when filled with an internal solution containing (mM): 110 $K^+$ aspartate, 20 KCl, 1 $MgCl_2$, 0.1 Na-GTP, 5 Mg-ATP, 5 $Na_2$-phosphocreatine, 5 EGTA, 10 HEPES, and pH adjusted to 7.3 with KOH. The external Tyrode's bath solution consisted of (mM): 140 NaCl, 5 KCl, 1 $MgCl_2$, 0.4 $KH_2PO_4$, 1.8 $CaCl_2$, 10 glucose, 5 HEPES, and pH adjusted to 7.4 with NaOH. Spontaneous electrical activity was measured whereas the iPSC-derived cardiomyocytes were left passive without current input. Twenty consecutive action potentials from spontaneously firing iPSC-derived cardiomyocytes were recorded to ensure stable waveforms for analysis. Data were corrected for the liquid junction potentials of +15.9 mV. Calcium transients were detected with confocal calcium imaging using a protocol described previously (Ng et al., 2010; J Mol Cell Cardiol 48, 1129-1137). Briefly, isolated iPSC-derived cardiomyocytes were loaded with 5 µM Fluo-3 AM (Invitrogen) for 25 minutes at 37° C. in Tyrode solution containing (mM): 140 NaCl, 5 KCl, 1 $MgCl_2$, 0.4 $KH_2PO_4$, 1.8 $CaCl_2$, 10 glucose, 5 HEPES at pH 7.4. Calcium transients were recorded with a confocal imaging system (Olympus Fluoview System version 4.2 FV300 TIEMPO) mounted on an upright Olympus microscope (IX71) and then quantified as background-subtracted fluorescence intensity changes normalized to the background subtracted baseline fluorescence. Data were fed into the Felix 32 (Photon Technology International) software for analysis.

i) Urine Collection and Cell Expansion

Appropriate containers (up to 500 ml) were sterilized before urine collection. Only the mid stream of urine was collected into sterile containers. The usual volume of specimens was 150-200 mL. Urine samples were then transferred inside a tissue culture hood into 50 mL tubes and these tubes were centrifuged at 400 g for 10 minutes at room temperature. The supernatant was carefully discarded inside a tissue culture hood, leaving approximately 1 mL or less of urine in the tube. Pellets were individually resuspended and all the 50 mL tubes derived from one sample collection were pooled into one single 50 mL tube. Around 10 mL of PBS containing ampothericin B and penicillin/streptomycin were added. The samples were centrifuged at 400 g for 10 minutes. The supernatant was discarded, leaving only around 0.2 mL of sample. Around 1 mL of primary medium was added to resuspend the cell pellet. The recipe of primary medium contained DMEM/Ham's F12 1:1 (Hyclone), 10% of fetal bovine serum (FBS; PAA), SingleQuot Kit CC-4127 REGM (Lonza), ampothericin B, and penicillin/streptomycin. The cells were transferred onto 12 well plates coated with L-gelatine in 1 mL of primary medium. The first 2 days a few hundred mL of primary medium were added to retain the antibiotics concentration and keep the nutrition level up. The following days the medium was carefully changed to REBM (Renal Epithelial Basal Medium, Lonza) medium containing SingleQuot Kit CC-4127 REGM (Lonza) (the combination of the two is referred to as urine cell medium), the procedure was never carried out completely to allow the presence of factors secreted by the urine cells and avoid unnecessary stress. Visible cells/colonies appeared routinely after 3-6 days. The first full media change was made after the first cells/colonies were seen. Cells were split onto a bigger surface aided by 0.25% trypsin containing 1 mM EDTA when the culture grew confluent. This and other procedures were approved by the ethics committee of the Guangzhou Institutes of Biomedicine and Health. RPTECs were generated as described by Wieser et al., 2008, Am J Physiol Renal Physiol 295, F1365-1375, and maintained in urine cell medium. Fibroblasts were obtained from skin fibroblasts purchased from Coriell cell repository and maintained in DMEM (Invitrogen) +10% (vol/vol) fetal bovine serum (FBS; Hyclone).

At first glance, urine cell cultures consisted mainly of squamous cells (likely from urethra) and a few blood cells (mostly erythrocytes), but after 2-3 days these cells disappeared and were substituted by small colonies (3 per sample on average) that grew quickly. These colonies corresponded to 2 main morphologies: type 1 or type 2, in agreement with previous reports on urine cell isolation (Dorrenhaus et al., Arch Toxicol 2000; 74, 618-626). Type 1 cells tended to be more rounded and grew closely attached to neighbour cells, suggestive of an epithelial phenotype. Type 2 cells were moderately more elongated and tended to grow a bit more dispersed. In some sample collections all colonies corresponded to 1 of the 2 types, but in others were mixed. These cell cultures were pooled upon reaching high density and split for further characterization or parallel reprogramming. Those enriched in type 1 cells displayed well-formed cell-cell junctions positive for E-cadherin and beta catenin (adherens junction markers), and ZO-1 (Zonula Occludens-protein 1; a tight junction marker), as assessed by immunofluorescence microscopy. They were as well positive for the intermediate filament keratin 7, an epithelial marker, and the renal proximal tubule marker CD13. Moreover, the distribution of actin was cortical rather than in stress fibers. Quantitative real-time PCR (qPCR) also supported a predominant epithelial origin as demonstrated by analysis of E-cadherin, occludin and claudin 1 (tight junction proteins), and the renal proximal tubule solute carrier family 2-transporter SLC2A1. Renal proximal epithelial cells (RPTECs; Wieser et al., 2008; Am J Physiol Renal Physiol 295, F1365-1375) and skin fibroblasts were used as positive and negative controls respectively for the immunofluorescence and qPCR. Type 2 cells-enriched cultures showed a rather similar immunofluorescence pattern but the intensity was milder and the distribution more patchy; qPCR results were likewise comparable. In both cases, little staining for the fibroblastic-like markers fibronectin and vimentin was observed.

ii) UiPSC Generation and Expansion

Samples from 12 young adults of either Chinese or Caucasian origin were reprogrammed, 7 corresponding to males and 5 to females. Urine cells at passages 2-3 were transduced with retroviruses that produce Sox2, Klf4, Oct4 and c-Myc (Cai et al., 2010; J Biol Chem 285, 11227-11234; Esteban et al., 2010; Cell Stem Cell 6, 71-79): Retroviral plasmids producing human Oct4, Sox2, Klf4 and c-Myc transcription factors were purchased from Addgene (Cambridge, Mass., USA). Viral supernatants were harvested on 2 consecutive days starting 48 hr after transfection. Urine cells at passages 2-4 were trypsinized and seeded on six-well dishes. 60,000 cells were added per well. Cells were infected with viral supernatants generated by transfection of 293T cells (using Lipofectamine 2000, Invitrogen) with retroviral pMXs vectors (Addgene) containing the cDNAs of human Oct4, Sox2, Klf4 and c-Myc. Two rounds of infection were performed successively (12 hours each). Polybrene (Sigma) was added to increase infection efficiency. After the second round of infection (infection efficiency was close to 100%, as demonstrated by control transduction with GFP-expressing vectors), the tissue culture medium of the transduced cells was changed to urine cell medium, and renewed daily. On day 3 or 4, cells were trypsinized and their number counted. Routinely, 50,000 cells were seeded onto a layer of feeders in a 10 cm culture dish and using human ESC medium (F12 [Invitrogen]+20% KSR [Knock-out Serum Replacement, Invitrogen]+10 ng/mL basic fibroblast growth factor+non essential aminoacids [Invitrogen], L-glutamine, and beta mercaptoethanol), which was renewed daily. On day 5, the medium was changed to human ESC medium+1 mM valproic acid (VPA; Sigma) or half ESC medium+half dFBS medium (consisting of DMEM high glucose [Invitrogen]+20% human defined fetal bovine serum [FBS, Hyclone]+VPA. VPA was only kept from day 5 to 12. the medium was changed to mTesR1 medium (Stemcell), and renewed daily until the last day of the experiment. From day 16, those colonies that were big enough and identifiable as human ESC-like (this is flat morphology with define borders and big nuclei containing prominent nucleoli), could be picked mechanically and expanded in human ESC medium on feeders or on mTesR1 medium on Matrigel.

iii) UiPSC Characterization

AP staining, transgene integration, karyotyping, and bisulfate sequencing were done as described by Cai et al., 2010; J Biol Chem 285, 11227-11234; Esteban et al., 2010; Cell Stem Cell 6, 71-79.

STR analysis was performed using an Applied Biosystems Genetic Analyzer (ABI3130, ABI). Genomic DNA was extracted using the DNeasy Tissue kit (Qiagen, Hilden, Germany) and total RNA was extracted using Trizol (Invitrogen, Paisley, USA). qPCR was performed using a Thermal Cycler Dice™ Real Time System (ABI7300, ABI, Foster, Calif., USA) and SYBR Green Premix EX Taq™ (Takara, Shiga, Japan); beta actin was used for normalization and all items were measured in triplicate. DNA microarrays were performed using Illumina's Human HT-12 V4.0 Expression Beadchip according to the manufacturer's instructions. Chips were scanned using Illumina BeadChip Reader and data analyzed using illumina BeadStudio Application. For teratomas, 2×10⁶ UiPSCs were injected subcutaneously or intramuscularly into the right hind leg of immuno-compromised NOD-SCID mice. Tumors were excised 8-10 weeks later, fixed, and embedded in paraffin, sectioned and stained with hematoxylin/eosin. For EB differentation, iPSCs on feeder were treated with dispase (Invitrogen) and collected by scraping. After centrifugation, cell pellets were re-suspended in human ESC medium without bFGF and grown for 8 days in non-adherent dishes. EBs were then transferred to gelatin-coated dishes to allow differentiation for another 8 days before processing for immunofluorescence analysis.

Characterization of the primary culture and the resulting UiPSCs showed that small colonies routinely appeared at days 9-16, this varying between donors without noticeable pattern. Many of these colonies progressively adopted human ESC-like morphology and were picked from day 16 to 25. The reprogramming efficiency also varied among donors, but in general was rather high, oscillating between 0.1% and 4%. UiPSCs were also produced from a 65 year old male individual, the reprogramming efficiency was lower (0.01%) but still significantly higher than reported for peripheral blood cells. Moreover, it was possible to freeze and thaw urine cells from several donors before transduction, and this did not impair reprogramming efficiency. Urine cells could also be infected at later passages albeit with a minor drop in efficiency.

After colony expansion, UiPSCs were characterized by standard procedures including alkaline phosphatase staining (AP), and showed clearly positive cell colonies with strong AP staining visualized by dark staining of the whole colony. These colonies further stained positive in indirect immunofluorescence staining for the ES markers TRA-1-60, TRA-1-81, Nanog, SSEA-3 and SSEA-4. Furthermore, qPCR for endogenous ESC genes plus silencing of these transgenes was observed. DNA microarrays demonstrated global gene expression close to H9 ESCs, since the arbitrary fluorescence units of the microarrays of the ES cells plotted against those of the UiPSCs show a linear slope of 45° angle. Single tandem repeat analysis (STR) of donor urine cells and UiPSCs showed matched origin in all cases. If the circumstances were such, the latter excludes the unlikely contamination and reprogramming of cells from a sexual partner.

After colony expansion, UiPSCs were characterized by standard procedures including alkaline phosphatase staining and showed clearly positive cell colonies with strong AP staining visualized by dark staining of the whole colony, while non-transfected cells did not show any staining for alkaline phosphatise. They showed a normal karyotype after transgene integration into the genomic DNA, and further stained positive in indirect immunofluorescence staining for the ES markers TRA-1-60, TRA-1-81, Nanog, SSEA-3 and SSEA-4. Furthermore, qPCR for endogenous ESC genes plus silencing of these transgenes (shown in the Table below; hTERT indicates human telomerase reverse transcriptase) was observed. Values are referred to donor urine cells; H9 ESCs were used as a control). DNA microarrays demonstrated global gene expression close to H9 ESCs since the arbitrary fluorescence units of the microarrays of the ES cells plotted against those of the UiPSCs show a linear slope of 45° angle. Bisulfite sequencing showed extensive demethylation in the Oct4 and Nanog proximal promoters in 2 representative UiPSC clones of the same donor. Single tandem repeat analysis (STR) of donor urine cells and UiPSCs showed matched origin and DNA microarrays demonstrated a global gene expression profile close to H9 ESCs.

|  | Donor cell | UC C0406-iPS C1P5 | UC C0406-iPS C4P7 | UC S0730-iPS 2P4 | UC S0730-iPS C3P4 | UC GZ0816-iPS C3P3 | UC ZGZ0816-iPS C4P2 | H9 ESCs |
|---|---|---|---|---|---|---|---|---|
| OCT4 | 1 | 110.43 | 120.98 | 101.28 | 91.59 | 153.20 | 108.96 | 269.94 |
| SOX2 | 1 | 992.36 | 1331.22 | 4195.71 | 3884.33 | 1651.03 | 1133.96 | 1587.38 |
| NANOG | 1 | 1178.53 | 856.14 | 111.00 | 113.12 | 1128.93 | 1172.23 | 402.32 |
| hTERT | 1 | 11964.73 | 14498.34 | 1311.36 | 1263.01 | 10149.00 | 7608.26 | 9768.02 | iv) Proving Multi-Differentiation Potential of UiPSCs

Figure 1:
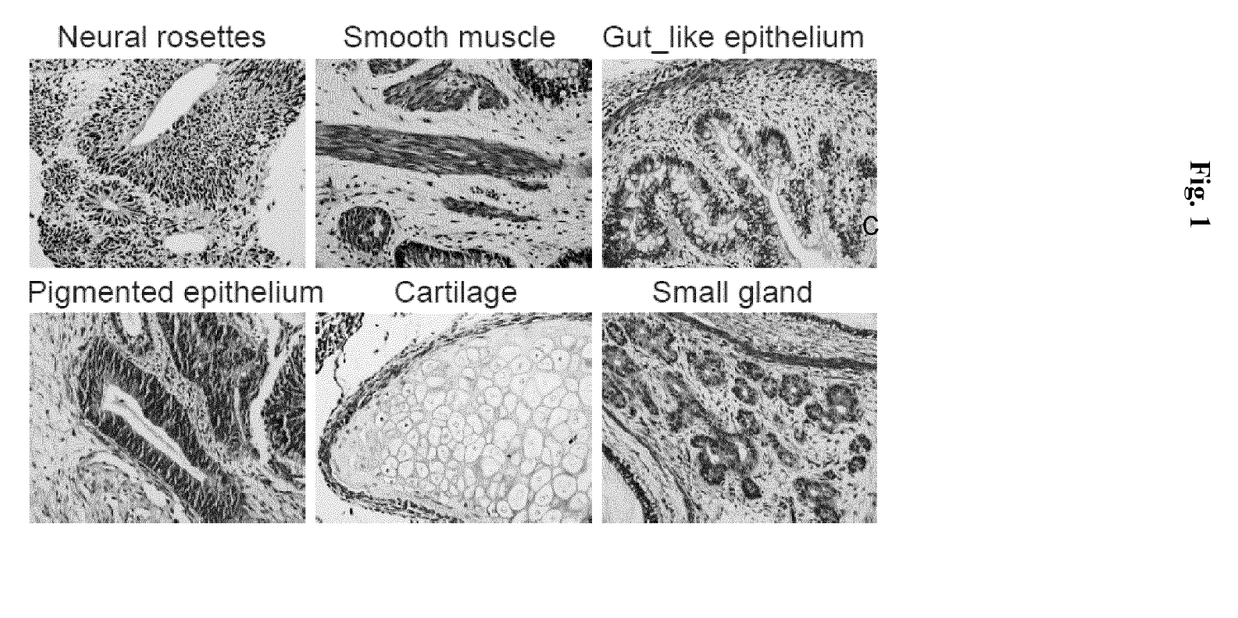
Figure 2:
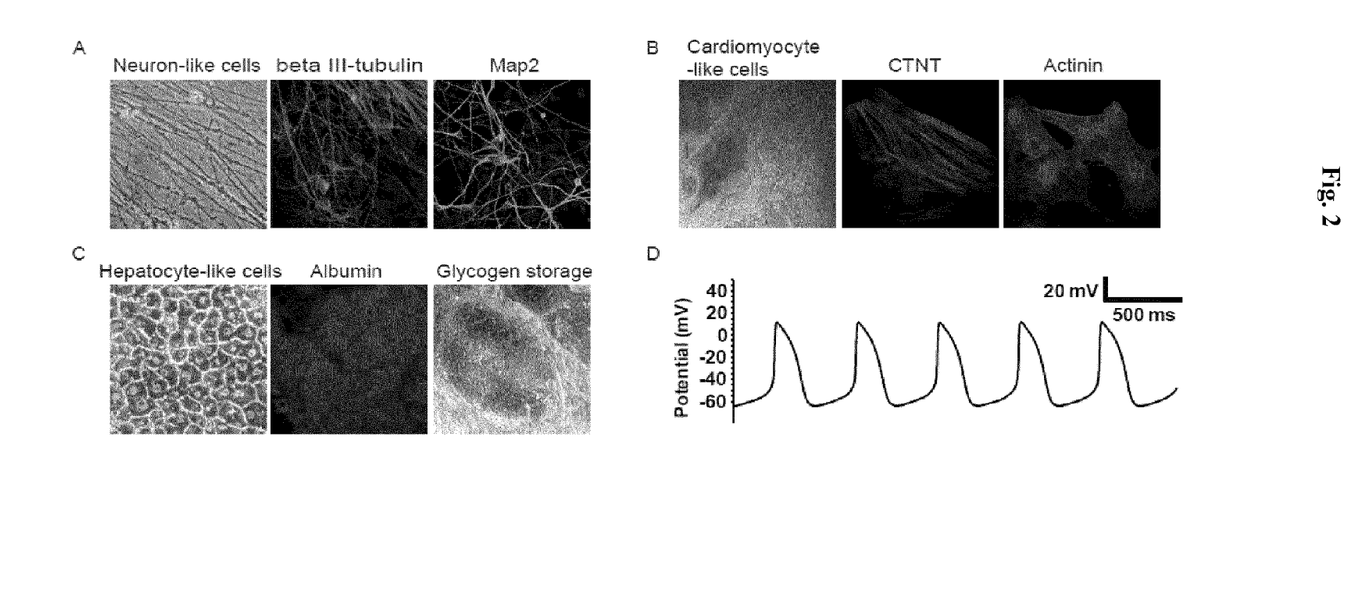

To prove that the UiPSCs are pluripotent, non-specific differentiation through teratoma (FIG. 1) and embryoid body (EBs) formation was performed. In both cases, the appearance of derivatives from the 3 germ layers was observed, and the teratomas contained rather complex structures without obvious sign of necrosis or invasion of the tumor capsule (FIG. 1). Then, directed UiPSC differentiation into neural lineages (neural stem cells, neurons and astrocytes) (FIG. 2A), cardiomyocytes (FIG. 2B) and hepatocytes (FIG. 2B); glycogen accumulation was detected with periodic acid Schiff's staining) was performed, which was verified by immunofluorescence microscopy for the appropriate markers and also qPCR (only for hepatocytes and cardiomyocytes). Noteworthy, neural differentiation was produced for 12 UiPSCs corresponding to 11 donors, hepatocytes for 4 clones of 3 donors, and cardiomyocytes for 14 clones of 11 donors. A video showed a high proportion of spontaneously beating EBs (between 30-75%). Likewise, electrophysiology measurement of action potentials (FIG. 2D) and calcium transients (electrophysiological properties of cardiomyocytes of two clones showed similar behavior to cardiomyocytes produced from human ESCs or fibroblast-derived iPSCs).

The invention claimed is:

1. A method for generating differentiated cells of interest from donor cells of another cell type, comprising:
    i) expanding exfoliated, terminally differentiated somatic cells isolated from urine; and
    ii) generating differentiated cells from said expanded cells by:
        a) reprogramming said expanded cells to become induced pluripotent stem cells (iPSCs); and
        b) differentiating said iPSCs into said cells of interest.

2. The method of claim 1, wherein said cells are selected from the group consisting of epithelial cells, fibroblastoid cells, and cancer cells.

3. The method of claim 1, wherein said reprogramming is effected by a mixture of exogenous reprogramming factors comprising factors selected from the group consisting of an Oct family gene, a Klf family gene, and a Sox family gene.

4. The method of claim 1, wherein said reprogramming is effected by a mixture of exogenous reprogramming factors comprising factors selected from the group consisting of Sox2, Oct4, Klf4, c-Myc and Nanog.

5. The method of claim 3, wherein said reprogramming involves expression of reprogramming factors by the cell without genomic integration and/or without expression of oncogenes.

6. The method of claim 3, wherein said reprogramming additionally comprises applying small molecules, small interfering RNAs or micro RNAs that increase efficiency of or replace one or more of said reprogramming factors.

7. The method of claim 1, wherein said cells are human cells.

8. A method for generating induced pluripotent stem cells (iPSCs), comprising:
    i. expanding exfoliated, terminally differentiated somatic cells isolated from urine, and
    ii. reprogramming said expanded cells to become iPSCs.

9. The method of claim 8, further comprising the step of differentiating said iPSCs into cells of interest.

* * * * *